United States Patent [19]

Dragan

[11] 4,198,756
[45] Apr. 22, 1980

[54] MANUAL EXTRUDER

[76] Inventor: William B. Dragan, R.D. #1 Burr St., Fairfield, Conn. 06430

[21] Appl. No.: 852,797

[22] Filed: Nov. 18, 1977

[51] Int. Cl.² .................................................. A61C 5/04
[52] U.S. Cl. ........................................ 222/326; 433/90
[58] Field of Search ................ 32/60; 222/326, 386; 128/234

[56] References Cited

U.S. PATENT DOCUMENTS

| 2,102,591 | 12/1937 | Hagemeier | 32/60 |
| 3,212,685 | 10/1965 | Swan et al. | 222/386 |
| 3,341,085 | 9/1967 | Sundholm | 222/326 |
| 3,900,954 | 8/1975 | Dragon | 32/60 |

FOREIGN PATENT DOCUMENTS

| 59028 | 9/1941 | Denmark | 128/234 |
| 483156 | 3/1917 | France | 222/386 |
| 1118081 | 6/1968 | United Kingdom | 222/386 |

Primary Examiner—Louis G. Mancene
Assistant Examiner—John J. Wilson
Attorney, Agent, or Firm—Arthur T. Fattibene

[57] ABSTRACT

A manual extruder for accurately and precisely extruding composite resin type material which includes an elongated tubular barrel having a readily detachable nozzle tip and an associated plunger for extruding the material to be dispensed from the nozzle tip. A pistol grip shaped handle is connected to the barrel and to which there is pivotally connected an actuating lever bearing on the plunger whereby the lever can be squeezed relative to the handle to provide the necessary mechanical advantage on the plunger for extruding the material with the use of one hand.

3 Claims, 6 Drawing Figures

MANUAL EXTRUDER

PROBLEM AND PRIOR ART

Efforts have been made to improve the manner in which certain viscous or heavy flowable material can be precisely and accurately extruded into small voids, e.g., in the field of dentistry wherein cavities are required to be filled with various types of composite resins. In industrial applications, it is frequently necessary to precisely dispense glues, adhesives, epoxies and various other paste-like materials to form or complete a finished product. Such materials generally have a very heavy consistency and tend to offer much resistance to applied pressures. This becomes more aggrevated when such materials are required to be dispensed through a very small aperture, as is frequently necessary for fine, precision work as in dentistry and/or in precision industrial application. Where the extrusions of such materials are required to be frequently dispensed manually by an operator e.g., in dentistry or in industry, the application of such material by known applicators is fatiguing and often difficult on the operator's hand. Accordingly, the present invention is directed to an improvement over my prior patented constructions as disclosed in U.S. Pat. Nos. 3,581,399 and 3,900,954 so as to overcome the problem of fatigue and/or resistance to applied pressure by the material being extruded or dispensed.

OBJECTS

An object of the present invention is to provide an improved manual extruder for accurately and precisely dispensing heavy flowable materials in a manner whereby maximum pressure can be imparted to the material to effect the extrusion thereof with a minimum of applied force being imparted thereto by an operator.

Another object resides in the provision of an improved manually operated extruder which is relatively simple in construction, inexpensive to manufacture, and which is positive in operation.

BRIEF SUMMARY OF INVENTION

The foregoing objects and other features and advantages are obtained by an improved extruder which comprises a tubular barrel or body having a plunger reciprocally disposed therein. The front of the barrel is provided with an opening for detachably receiving a nozzle tip through which the material to be dispensed is extruded. The barrel is fixedly secured to a pistol shaped handle grip whereby a portion of the handle grip extends above and below the barrel. Connected to the handle grip by a suitable pivot is a lever which is adapted to engage the end of the plunger. A spring normally biases the plunger toward the retracted or inoperative position. The arrangement is such that upon the application of a squeezing force on the operating lever and the handle grip, the plunger is displaced to extrude the material through the nozzle tip. The nozzle tip is provided with a very fine aperture opening so that an accurate and precise dispensing of the material can be effected.

FEATURES

A feature of this invention resides in the provision of a manual hand operated extruder for accurately dispensing heavy viscous paste-like material through a very fine aperture opening by a squeezing action with one hand.

Another feature of this invention resides in the provision of a manual extruder having combination handle grip and actuating lever operatively connected to the barrel and plunger respectively whereby a mechanical advantage is obtained for precisely extruding an extrudant in accordance with a desired precision.

Other features and advantages will become more readily apparent when considered in view of the detail description and drawings in which.

DETAILED DESCRIPTION

Figure 1:
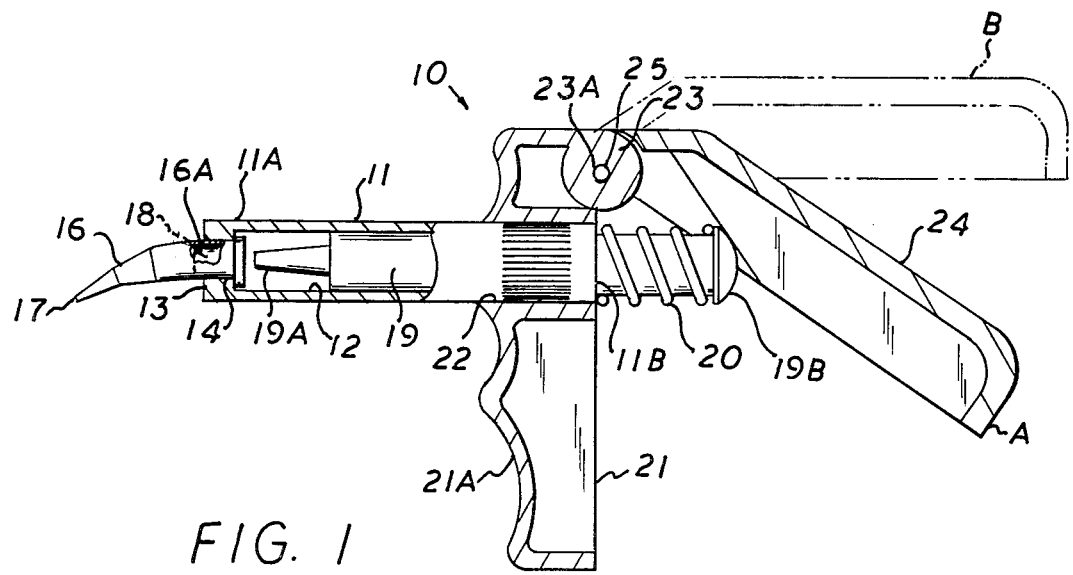
FIG. 1 is a side elevation view of a manual extruder embodying the present invention with parts shown in section.

Referring to the drawings, there is shown in FIG. 1 a manual extruder 10 embodying the present invention. The extruder 10 is especially adapted for dispensing and/or extruding heavy viscous, past-like materials, such as composite resins of the type used in dentistry to fill cavities for tooth restorations; or for use in industry to dispense glues, expoxies, adhesives and the like. As will be hereinafter set forth, the construction of the extruder 10 is such that it can be hand operated with one hand in a manner whereby a minimum of physical force is required to effect the dispensing operation, while at the same time, enabling an operator or dentist to effect an accurate and precise dispensing operation.

The extruder 10 comprises a tubular barrel 11 having a bore 12 extending therethrough. The front end 11A of the barrel 11 is provided with an inturned flange or lip 13 to define a front opening 14. A side portion of the barrel adjacent the front opening 14 is formed with a breech opening 15.

A nozzle tip 16 is detachably connected to the front opening 14 of the barrel. The nozzle tip may be of the type described and disclosed in my U.S. Pat. No. 3,581,399 or 3,900,954. Essentially, the nozzle tip is provided with a body portion 16A which is adapted to contain a supply of the material to be dispensed or extruded. The body portion 16 diverges to define a very fine or small discharge orifice 17. A piston 18 is slideably disposed in the body portion 16A of the nozzle tip whereby upon displacement of the piston within the body 16A of the nozzle tip, the material in advance thereof is extruded.

To effect displacement of piston 18, there is slideably disposed within the barrel a plunger 19. The plunger 19 is provided with a diameter which is slideably received within the bore 12 of barrel 11. The front of the plunger 19 is provided with a reduced projection 19A which is adapted to be received within the body 16A of the nozzle tip 16 when the plunger is shifted to a protracted position, as will be hereinafter described.

The rear end of the plunger 19 is provided with an enlarged head end 19B which normally extends beyond the rear end of the barrel 11. A coil spring 20 is disposed about the extended end portion of the plunger 19 to normally bias the plunger towards its retracted or inoperative position as seen in FIG. 1.

It will thus be noted that the spring 20 is engaged between the rear end 11B of barrel 11 and the flange defined by the enlarged head end 19B of the plunger 19.

In accordance with this invention, a handle means 21 is connected to the barrel 12. In the illustrated embodiment, the handle means comprises a pistol shaped grip wherein the front wall portion 21A may be sculptured to provide finger rests. As shown, the pistol grip member is provided with an opening 22 disposed intermediate the ends for receiving the rear end portion of barrel 11. The barrel is suitably fixed to the handle 21 by any suitable means, such as bonding, welding, friction, swedging and the like.

The intermediate location of the barrel 11 relative to the handle grip 21 is such that an operator may conveniently hold the barrel 11 of the extruded between the first and middle fingers which will facilitate the operator's handling and operation of the extruder.

Figure 4:
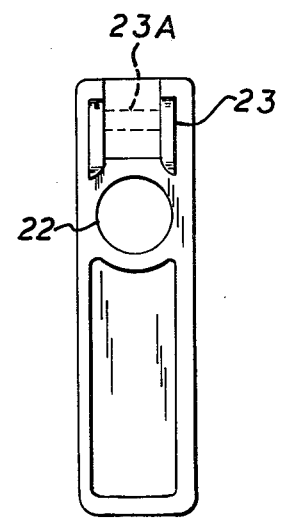
FIG. 4 is a detail end view of the pistol grip handle member.

The upper end of grip 21 is provided with a central lug 23 to define a bearing or pivot for an operating handle or lever 24. As best seen in FIGS. 1 and 4, the lug 23 is provided with a hole 23A for accommodating a pivot pin for the lever 24.

Figure 5:
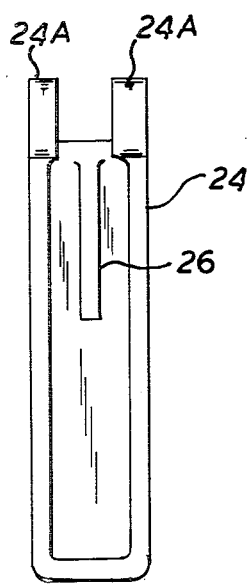
FIG. 5 is a detail end view of the actuating lever.
Figure 6:
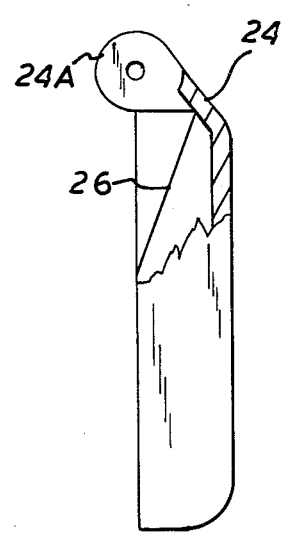
FIG. 6 is a detail side view of the actuating lever having portions broken away.

As best seen in FIG. 5, the upper end of lever 24 is provided with a pair of spaced ear portions 24A—24A which are adapted to straddle the central lug 23 of the hand grip 21. The respective ear portions 24A, 24A are provided with aligned holes arranged to align with hole 23A whereby a pivot pin 25 extended through the aligned holes pivotally secures the lever 24 to handle grip 21.

The lever 24 intermediate the width thereof is provided with a cam 26 which is arranged to cam against the head 19B of the plunger 19. It will be noted that the lever is loosely pivoted relative to the hand grip 21. The complementary bearing surfaces of the lug 23 and the ear portions 24A, 24A of lever 24 are such so as to permit the lever to be pivoted upwardly to position B as shown in FIG. 1. In this position, the plunger 19, if desired, can be readily removed for cleaning or repair.

Figure 2:
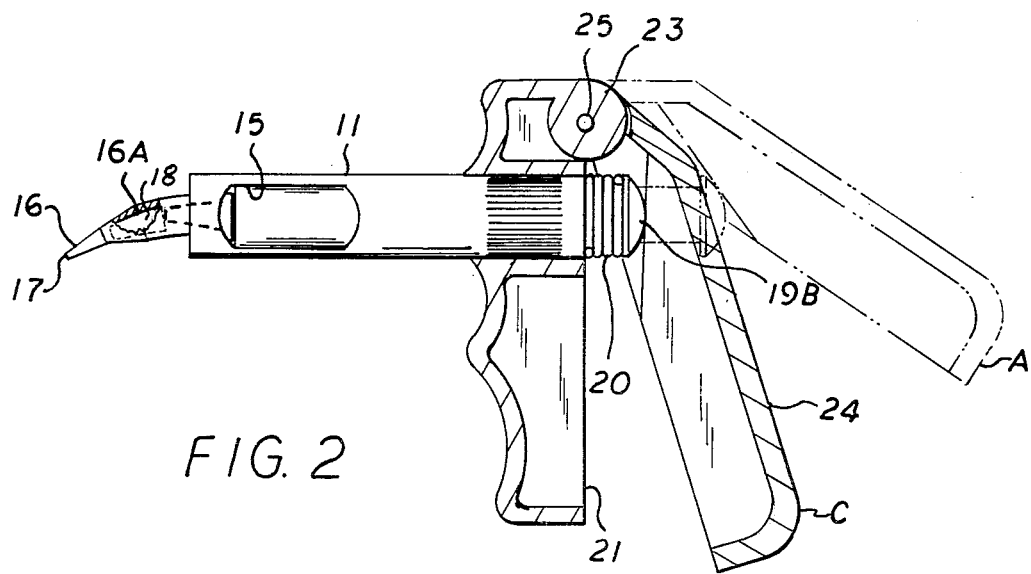
FIG. 2 is a side view similar to FIG. 1 showing the parts of an operative extruding position.
Figure 3:
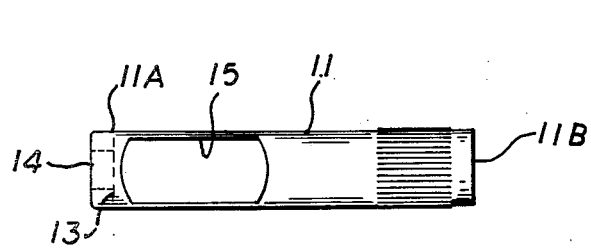
FIG. 3 is a detail side elevation view of the barrel portion of the extruder.

Position A of the lever as indicated in FIG. 1 illustrates the normal, retracted or inoperative position of the respective component parts. Position C of the lever as shown in FIG. 2 illustrates the component parts in the protracted or operative extruding position.

In operation, the extruder described operates as follows:

The material to be dispensed is loaded into the body or reservoir position 16A of the nozzle tip 16 and the piston 18 positioned within the tip to seal the body portion. The tip loaded is inserted through the breech opening 15 so as to be extended through the front opening 14 of the barrel 11. The breech loading of the nozzle tip can be readily accomplished with the plunger 19 normally in a retracted position.

With the tip 16 loaded and in place in the barrel 11, the extruder is then gripped in the palm of one's hand with the barrel 11 disposed between the operator's first and middle fingers. By exertion of a squeezing action, the palm of the operator's hand causes the lever 24 to be squeezed toward the grip portion 21, whereby the camming action between the wedge or edge 26 effects a displacement of the plunger 19 toward its protracted position. As the tip 19A of the plunger advances into the nozzle tip 16, the position 18 is advanced into the body 16A of the nozzle, thereby causing the material in advance of the piston 18 to be extruded through the fine orifice opening 17.

With the construction and operation described, an operator can maintain accurate control over the extruding operation, and the lever and cam action defined cooperate to provide the operator with the mechanical advantage desired so that the resistance of the paste-like material discharging through a fine orifice opening 17 can be effectively overcome with a minimum of applied manual pressure or squeezing force; and at the same tine, enabling the operator to maintain precise control over the amount and speed at which the material is extruded through the orifice opening 17.

While the foregoing invention has been described with respect to a particular embodiment thereof, it will be appreciated and understood that variations and modification may be made without departing from the spirit or scope of the invention.

What is claimed is:

1. A manual extruder for extruding composite resins for use in dentistry comprising:
   an elongated tubular barrel, said barrel having a front and rear end,
   said front end having an inturned flange defining a front opening,
   said barrel having a side breech opening adjacent said front end,
   a plunger reciprocally mounted in said barrel for movement between a retracted and protracted position, said plunger extending into the rear end of said barrel whereby said plunger is readily insertable into and removed from the rear end of said barrel,
   a handle means connected to said barrel so as to permit the insertion and removal of said plunger from the rear of said barrel,
   said handle means including a pistol grip shaped member having a barrel opening disposed intermediate the ends of said member,
   said barrel opening being sized for accommodating said rear end of said barrel whereby said pistol grip member is disposed normal and intermediate to the longitudinal axis of said barrel so that said pistol grip member extends to either side of said longitudinal axis,
   means for fixedly securing said barrel in said barrel opening to said gripping member whereby said barrel is adapted to be disposed between the first and middle finger of an operator when in use,
   an actuating lever pivotally connected directly to one end of said pistol grip member for movement toward and away from said pistol grip member,
   a spring means for normally biasing said plunger toward the retracted position,
   said lever having a cam surface thereon disposed in engagement with said plunger whereby the movement of said lever toward said pistol grip member effects displacement of said plunger toward the protracted position,
   and a readily detachable nozzle tip extending through the front opening of said barrel,
   said nozzle tip only being adapted to contain a supply of composition resin,
   a piston slideably disposed in said nozzle tip,
   and said plunger having a forwardly extended projection for engaging said piston to effect the displacement thereof for extruding the supply of composite resin disposed in said nozzle tip when said actuating lever is moved toward said pistol grip member.

2. A manual extruder as defined in claim 1 and including means to limit the movement of said lever relative to said pistol grip member between the retracted and protracted position of said plunger.

3. A manual extruder for extruding heavy paste-like materials for use in dentistry comprising:

an elongated tubular barrel, said barrel having a front end, an open rear end and a bore extending therethrough, said front end having an inturned flange defining a front opening, said barrel having a side breech opening adjacent said front end, a plunger extending into and beyond the open rear end of said barrel and reciprocally mounted in the bore of said barrel for movement between an operative and inoperative position whereby said plunger is readily insertable into and removeable from the rear end of said barrel, said plunger having an enlarged head end portion extending beyond the rear end of said barrel, handle means connected to said barrel whereby said handle means includes a, handle grip having a hole intermediate the length thereof for receiving the rear end of said barrel, whereby said handle grip is disposed normal to the axis of said barrel, means for fixedly securing the barrel to said handle grip, whereby said handle grip extends above and below said barrel so that said barrel is disposed between an operator's first and second finger when in use, an actuating lever pivotally connected to the upper end of said handle means for movement toward and away from said handle means, a spring for normally biasing said plunger toward an inoperative position against said lever, said handle grip having a fixed lug adjacent the upper end thereof, said lever having a pair of spaced apart ear portions, said ear portions straddling said lug therebetween, means for pivotally connecting said lever ear portions to said lug portion, said lever having a cam thereon, said cam having a inclined surface relative to said plunger head and being disposed in direct engagement with the head of said plunger whereby the movement of said lever relative to said handle grip effects displacement of said plunger toward operative position and whereby said plunger is rendered readily removeable independently of said handle means, a readily expendible nozzle tip extending through the front opening of said barrel, said nozzle tip having a body portion for containing a supply of material to be dispensed, said nozzle tip having a discharge opening, a piston slideably disposed in the body portion of said nozzle tip, said plunger having a reduced tip portion projecting toward the front end of the barrel, said reduced tip portion engaging said piston to effect displacement thereof within said body portion of said nozzle tip when said plunger is advanced to the protracted, operative position whereby said piston extrudes the material through said discharge opening as said lever is displaced toward said fixed handle grip.

* * * * *